(12) United States Patent
Franke et al.

(10) Patent No.: US 6,939,335 B2
(45) Date of Patent: Sep. 6, 2005

(54) AESTHETICALLY IMPROVED SIDE PANELS FOR DISPOSABLE GARMENTS AND METHODS OF MAKING THE SAME

(75) Inventors: Mark S. Franke, Neenah, WI (US); Cynthia Louise Wyngaard, Kaukauna, WI (US); Heather S. Mortell, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 28 days.

(21) Appl. No.: 10/027,235

(22) Filed: Dec. 20, 2001

(65) Prior Publication Data

US 2003/0120254 A1 Jun. 26, 2003

(51) Int. Cl.⁷ .................................................. A61F 13/15
(52) U.S. Cl. ...................... 604/396; 604/394; 604/386; 604/387; 604/389; 604/393
(58) Field of Search ........................... 604/396, 385.01, 604/386, 387, 389, 390, 393, 394; 24/442–450

(56) References Cited

U.S. PATENT DOCUMENTS

| | | | |
|---|---|---|---|
| 3,338,992 A | 8/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,205,679 A | 6/1980 | Repke et al. | |
| 4,340,563 A | 7/1982 | Appel et al. | |
| 4,610,681 A | 9/1986 | Strohbeen et al. | |
| 4,646,362 A | 3/1987 | Heran et al. | |
| 4,663,220 A | 5/1987 | Wisneski et al. | |
| 4,704,116 A | 11/1987 | Enloe | |
| 4,747,846 A | 5/1988 | Boland et al. ............ 604/38 A |
| 4,909,804 A | 3/1990 | Douglas, Sr. | |
| 4,938,757 A | 7/1990 | Van Gompel et al. | |
| 4,940,464 A | 7/1990 | Van Gompel et al. | |
| 5,046,272 A | 9/1991 | Vogt et al. | |
| 5,074,854 A | 12/1991 | Davis | |
| 5,104,116 A | 4/1992 | Pohjola | |
| 5,224,405 A | 7/1993 | Pohjola | |
| 5,226,992 A | 7/1993 | Morman | |
| 5,236,430 A | 8/1993 | Bridges | |
| 5,246,433 A | 9/1993 | Hasse et al. | |
| 5,569,234 A | 10/1996 | Buell et al. | |
| 5,618,366 A | 4/1997 | Suekane | |
| 5,662,638 A | 9/1997 | Johnson et al. | |
| 5,779,831 A | 7/1998 | Schmitz | |
| 5,786,058 A | 7/1998 | Megchelsen et al. | |
| 5,855,574 A * | 1/1999 | Kling et al. ................ 604/392 |
| 5,876,394 A | 3/1999 | Rosch et al. ................ 604/393 |
| 6,042,673 A | 3/2000 | Johnson et al. | |
| 6,079,343 A | 6/2000 | Wong | |
| 6,120,489 A | 9/2000 | Johnson et al. | |
| 6,149,637 A | 11/2000 | Allen et al. ................ 604/366 |
| 6,213,991 B1 * | 4/2001 | Kling et al. ............ 604/385.01 |

FOREIGN PATENT DOCUMENTS

| | | |
|---|---|---|
| EP | 0 217 032 | 4/1987 |
| EP | 0 635 248 A1 | 1/1995 |
| GB | 2 071 564 A | 9/1981 |
| WO | 96/16220 | 5/1996 |
| WO | 99/60966 | 12/1999 |
| WO | 99/60971 | 12/1999 |
| WO | 00/35395 | 6/2000 |
| WO | WO 01/79602 | 10/2001 |

OTHER PUBLICATIONS

*Vogue Elements*, Butterick Company, Inc. (2 pages), 1997.

* cited by examiner

*Primary Examiner*—Jacqueline F. Stephens
(74) *Attorney, Agent, or Firm*—Pauley Petersen & Erickson

(57) ABSTRACT

A pant-like absorbent garment having side seams extending from a waist opening to each of two leg openings between a front side panel and a back side panel. The side seams are offset or folded to conceal the post-bonding edges and provide a finished or aesthetically pleasing appearance.

22 Claims, 6 Drawing Sheets

AESTHETICALLY IMPROVED SIDE PANELS FOR DISPOSABLE GARMENTS AND METHODS OF MAKING THE SAME

FIELD OF THE INVENTION

This invention is directed to side seams for a disposable personal care garment having a discreet or aesthetically pleasing appearance.

BACKGROUND OF THE INVENTION

Pant-like absorbent garments, such as adult incontinence wear as well as infant and children's diapers, swim wear and training pants, typically have a front side panel and a back side panel which are joined together at a side seam to provide a complete side panel. In some garments, the side panels are connected at the side seam using a conventional ultrasonic process, whereby the inside surface of the front side panel is bonded to the inside surface of the back side panel. The excess material can be trimmed or removed from the bond area, leaving edge portions having approximately equal length. However, the resulting side seam and edge portions of the front side panel and back side panel protrude outwardly from the side of the garment, making the side seam appear unfinished or not aesthetically pleasing.

There is a need or desire for disposable personal care garments that have side seams which reduce the amount of side panel material that protrudes outwardly from the side of the garment after the front side panel is bonded to the back side panel.

There is a need or desire for disposable personal care garments that have side seams which connect the front side panel and back side panel together and provide a more aesthetically pleasing appearance.

SUMMARY OF THE INVENTION

The present invention is directed to disposable personal care garments having side seams which connect a front side panel to a back side panel to form a complete side panel having an aesthetically pleasing appearance. The present invention reduces the outward protrusion of the side seam by off-setting the excess post-bonding edges and bonding the edges flat to the side panel or folding the excess post-bonding edges to conceal them from the outside and inside panel surface to provide a more aesthetically pleasing side seam.

Each side seam includes an edge portion of a front side panel and an edge portion of a back side panel. The edge portions are bonded together using a bonding pattern which provides a primary bond. The side seams can extend from a waist opening to each of two leg openings between a front side panel and a back side panel.

In one embodiment of this invention, the side seam is folded flat along one of a front side panel and a back side panel. The longer excess edge covers the shorter excess edge. The side seam is bonded to the side panel desirably using adhesive bonds and/or ultrasonic bonds to maintain the fold in proper position against the side panel. The primary side seam bond pattern faces out from the garment and can be modified to be less noticeable. For example, a series of folds and secondary bonds can conceal the cut edges and maintain the folded material in position.

With the foregoing in mind, it is a feature and advantage of the invention to provide a secured side seam for a disposable personal care garment that has an aesthetically pleasing appearance.

DEFINITIONS

Figure 1:
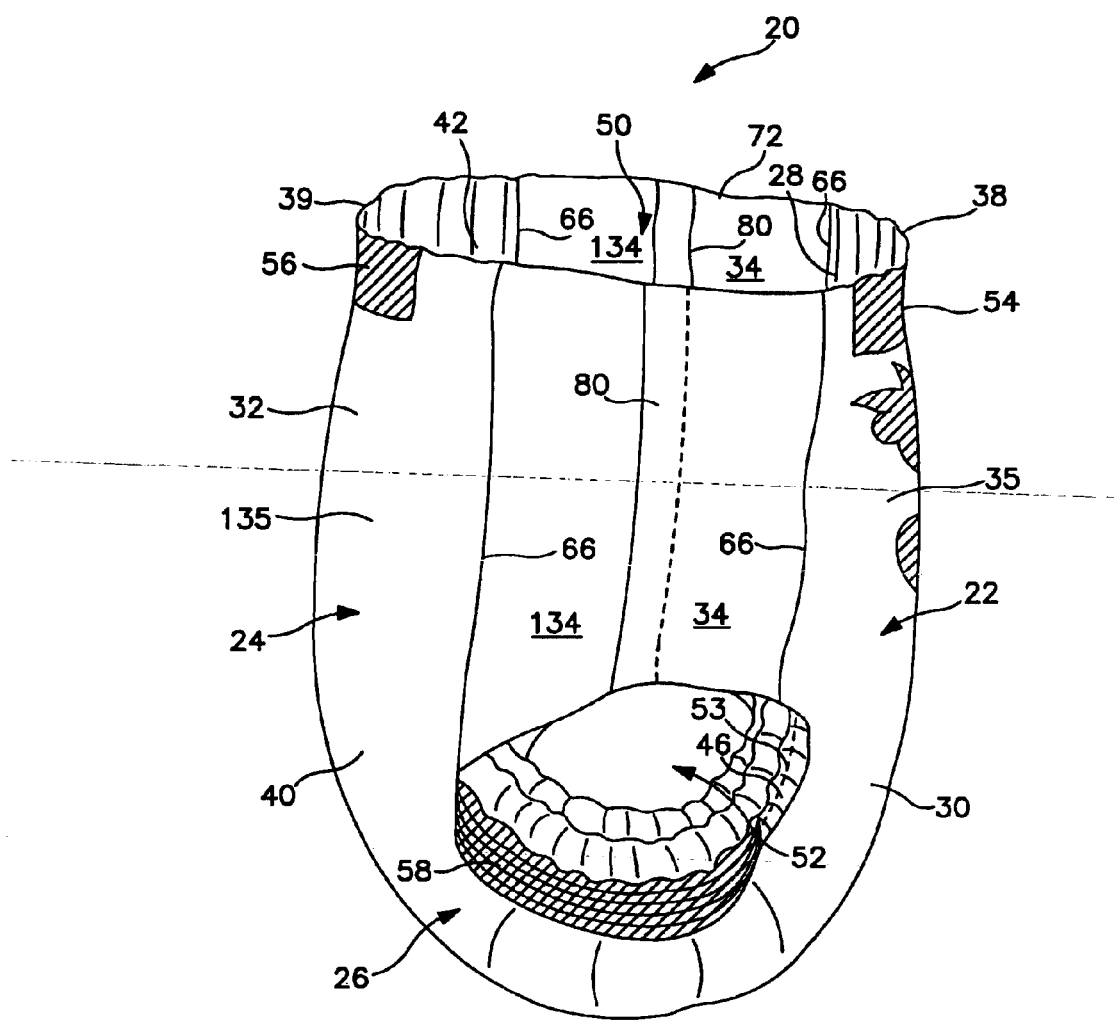
FIG. 1 is a side perspective view of a disposable garment having side seams, according to one embodiment of this invention.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Concealed" refers to a material which is enveloped within the surrounding materials such that it is not visible from either an interior or exterior of the product.

"Connected" refers to the joining, adhering, bonding, attaching, or the like, of two elements. Two elements will be considered to be connected together when they are connected directly to one another or indirectly to one another, such as when each is directly connected to intermediate elements.

"Cross direction" refers to the width of a fabric in a direction generally perpendicular to the direction in which it is produced, as opposed to "machine direction" which refers to the length of a fabric in the direction in which it is produced.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Flexible" refers to materials which are compliant and which will readily conform to the general shape and contours of the wearer's body.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Integral" or "integrally" is used to refer to various portions of a single unitary element rather than separate structures bonded to or placed with or placed near one another.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 3:
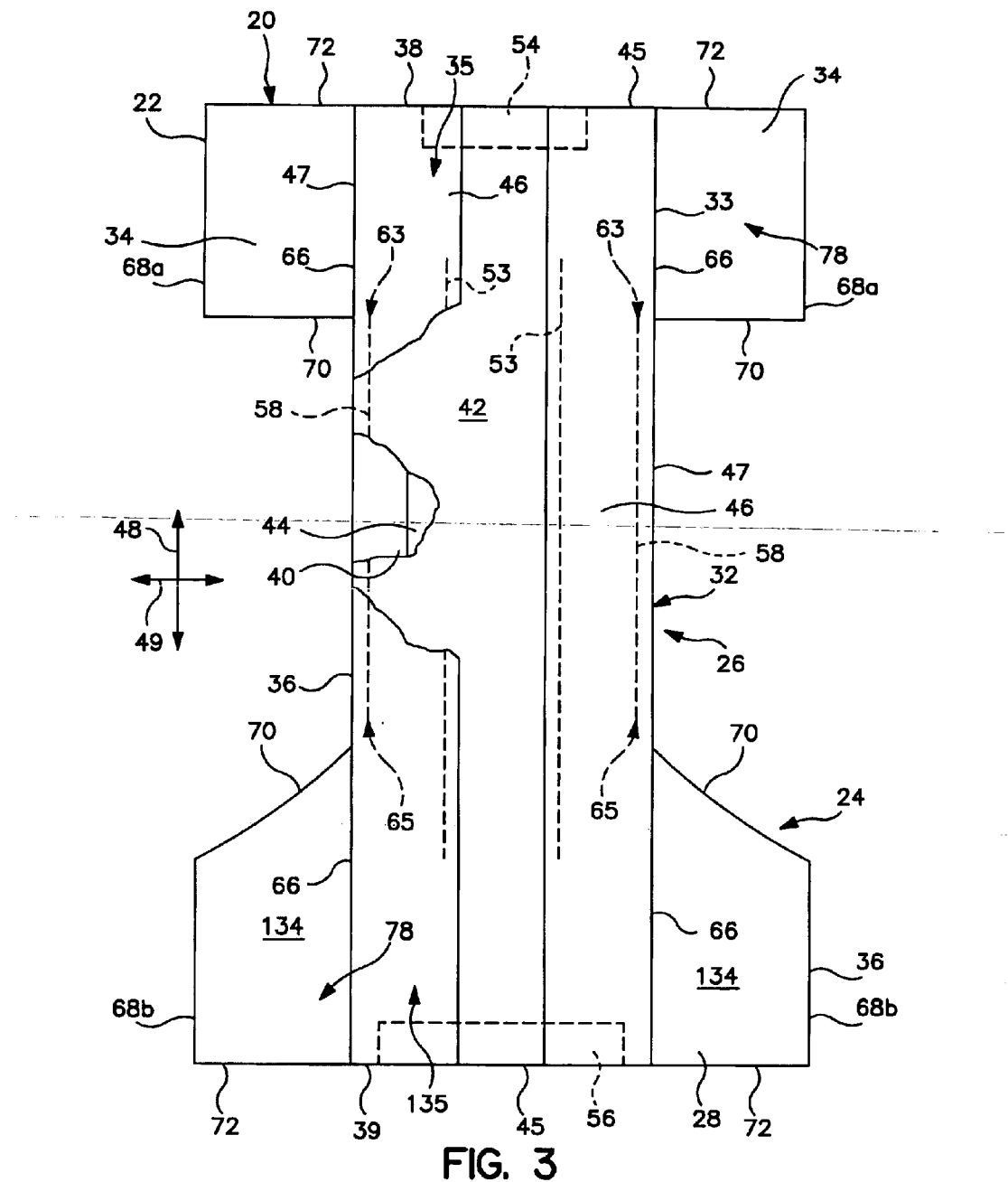
FIG. 3 is a plan view of the disposable garment of FIGS. 1 and 2 in a partially disassembled, stretched flat state, and showing the surface of the garment that faces the wearer when the article is worn, and with portions cut away to show the underlying features, according to one embodiment of this invention.

"Longitudinal" and "transverse" have their customary meaning, as indicated by the longitudinal and transverse axes depicted in FIG. 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Machine direction" refers to the length of a fabric in the direction in which it is produced, as opposed to "cross direction" which refers to the width of a fabric in a direction generally perpendicular to the machine direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Offset" refers an edge of a first material, for example a first side panel, extending in a direction, such as a lateral direction, further than a corresponding edge of a second material, for example a second side panel.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Primary bond" refers to a joining, adhering, connecting, attaching, or the like, of two elements. The primary bond may be applied to the elements using any suitable bonding means including, but not limited to, adhesive bonding means and ultrasonic bonding means. Desirably, the primary bond is a permanent bond and may include a single bond or a plurality of bonds.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Secondary bond" refers to a joining, adhering, connecting, attaching, or the like, of two elements, subsequent to a primary bond. Like a primary bond, the secondary bond may be applied to the elements using any suitable bonding means including, but not limited to, adhesive bonding means and ultrasonic bonding means. Desirably, the secondary bond is a permanent bond and may include a single bond or a plurality of bonds.

"Shearing strain" refers to forces that tend to produce an opposite but parallel sliding motion between two bodies' planes.

"Side Seam" refers to a region on a pant-like disposable garment where a front side panel is connected to a back side panel to form a prefastened, pant-like garment.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to a disposable garment having side seams which are offset or folded to conceal the post-bonding edges.

The principles of the present invention can be incorporated into any suitable disposable pant-like garment, including but not limited to, a disposable absorbent article. Examples of such suitable articles include diapers, training pants, feminine hygiene products, incontinence products, other personal care garments, disposable clothing, health care garments, or the like. For ease of explanation, the description hereafter will be in terms of a child's training pant.

Referring to FIG. 1, a disposable article, such as a training pant 20, is illustrated in a fastened condition. The training pant 20 includes an absorbent chassis 32. The absorbent chassis 32 defines a front region 22, a back region 24, a crotch region 26 interconnecting the front region 22 and the back region 24, an inner surface 28 which is configured to contact the wearer, and an outer surface 30 opposite the inner surface 28 which is configured to contact the wearer's clothing. With additional reference to FIGS. 2 and 3, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39.

Figure 2:
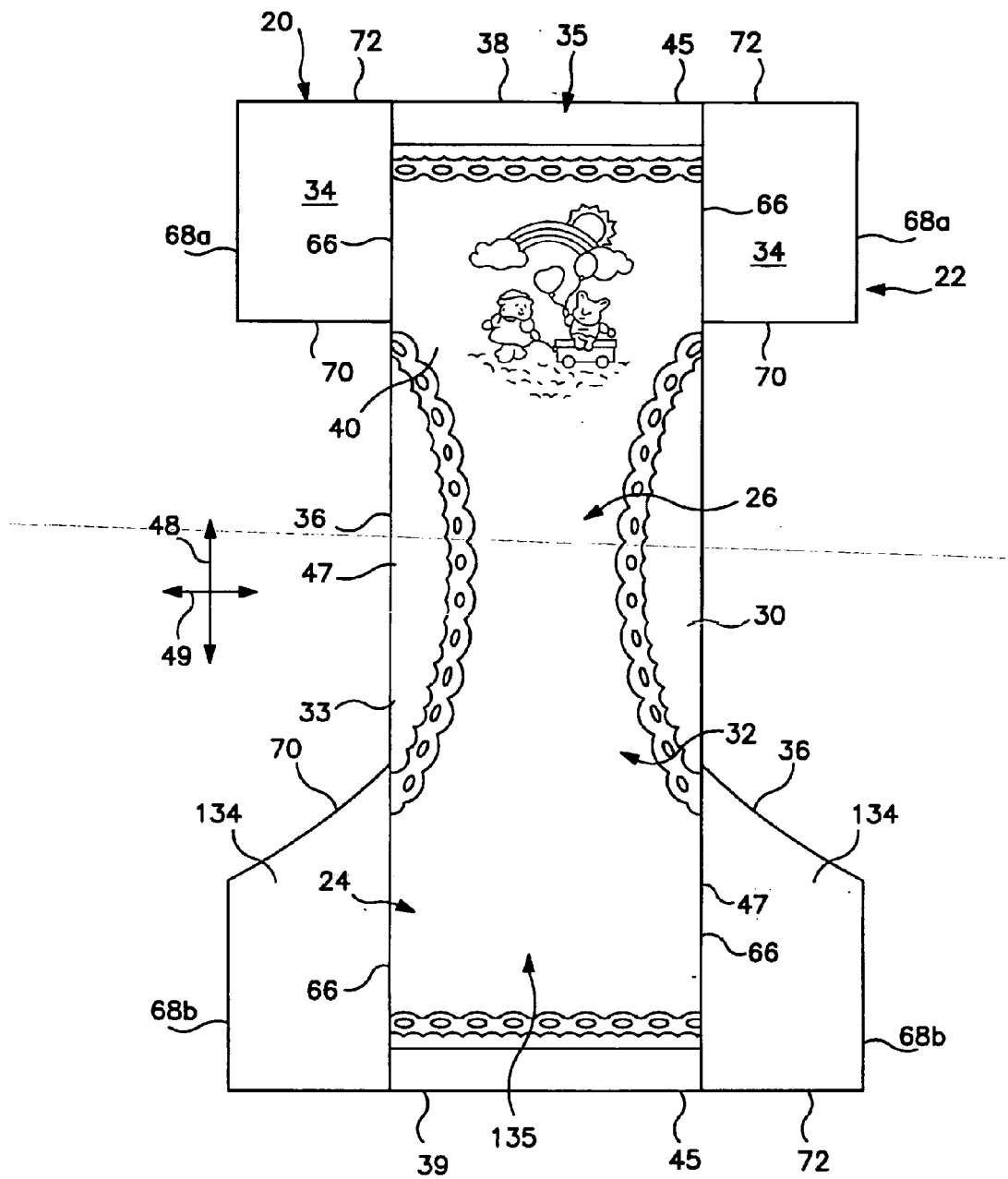
FIG. 2 is a plan view of the disposable garment of FIG. 1 in a partially disassembled, stretched flat state, and showing the surface of the garment that faces away from the wearer when the garment is worn, according to one embodiment of this invention.

The illustrated absorbent chassis 32 includes a somewhat rectangular composite structure 33, a pair of transversely opposed front side panels 34, and a pair of transversely opposed back side panels 134. The composite structure 33 and side panels 34 and 134 may be integrally formed or may include two or more separate elements, as shown in FIGS. 2 and 3. The illustrated composite structure 33 includes an outer cover 40, a bodyside liner 42 which is connected to the outer cover in a superposed relation, an absorbent core 44 (FIG. 3) which is located between the outer cover 40 and the bodyside liner 42, and a pair of containment flaps 46 (FIG. 3). The somewhat rectangular composite structure 33 has opposite end edges 45 that form portions of the front and back waist edges 38 and 39, and opposite side edges 47 that form portions of the side edges 36 of the absorbent chassis 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as illustrated in FIG. 1, the front region 22 and the back region 24 are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front side panels 34 and the back side panels 134 include the portions of the training pant 20 which, when worn, are positioned on the hips of the wearer.

The front region 22 of the absorbent chassis 32 includes the transversely opposed front side panels 34 and a front center panel 35 (FIGS. 2 and 3) positioned between and interconnecting the side panels, along with a front waist elastic member 54 and any other connected components. The back region 24 of the absorbent chassis 32 includes the transversely opposed back side panels 134 and a back center panel 135 (FIGS. 2 and 3) positioned between and interconnecting the side panels, as well as a rear waist elastic member 56 and any other connected components. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably, although not necessarily, includes the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis 32 or may only extend partially along the length of the absorbent chassis 32. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes the front waist elastic member 54, the rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E. I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a as nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 is illustrated as overlying the outer cover 40 and absorbent core 44, and may but need not have the same dimensions as the outer cover 40. The bodyside liner 42 is desirably compliant, soft feeling, and non-irritating to the child's skin. Further, the bodyside liner 42 can be less hydrophilic than the absorbent core 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbond web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 from Uniqema Inc., a division of ICI of New Castle, Del., U.S.A. and GLUCOPON® 220UP from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent core 44 include materials that are generally not elastomeric.

The absorbent core 44 (FIG. 3) is positioned between the outer cover 40 and the bodyside liner 42, which components can be joined together by any suitable means, such as adhesives, as is well known in the art. The absorbent core 44 can be any structure which is generally compressible, conformable, non-irritating to the child's skin, and capable of absorbing and retaining liquids and certain body wastes. The absorbent core 44 can be manufactured in a wide variety of sizes and shapes, and from a wide variety of liquid absorbent materials commonly used in the art. For example, the absorbent core 44 can suitably include a matrix of hydrophilic fibers, such as a web of cellulosic fluff, mixed with particles of a high-absorbency material commonly known as superabsorbent material. In a particular embodiment, the absorbent core 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be non-uniformly mixed. The fluff and superabsorbent particles can also be selectively placed into desired zones of the absorbent core 44 to better contain and absorb body exudates. The concentration of the superabsorbent particles can also vary through the thickness of the absorbent core 44. Alternatively, the absorbent core 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent core 44 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent core 44 in an amount of from about 0 to about 90 weight percent based on total weight of the absorbent core 44. The absorbent core 44 suitably has a density within the range of about 0.10 to about 0.50 grams per cubic centimeter. The absorbent core 44 may or may not be wrapped or encompassed by a suitable tissue wrap that maintains the integrity and/or shape of the absorbent core 44.

The absorbent chassis 32 can also incorporate other materials that are designed primarily to receive, temporarily store, and/or transport liquid along the mutually facing surface with the absorbent core 44, thereby maximizing the absorbent capacity of the absorbent core 44. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded to the composite structure 33 of the absorbent chassis 32 in the respective front and back regions 22 and 24, and are attached or connected to one another at a side seam 80. The front side panel 34 and back side panel 134 can be releasably attached or can be permanently bonded together. More particularly, as shown best in FIGS. 2 and 3, the front side panels 34 can be permanently bonded to and extend transversely beyond the side edges 47 of the composite structure 33 in the front region 22 along attachment lines 66, and the back side panels 134 can be permanently bonded to and extend transversely beyond the side edges of the composite structure in the back region 24 along attachment lines 66. The side panels 34 and 134 may be attached to the composite structure 33 and to each other using attachment means known to those skilled in the art such as adhesive bonding, thermal bonding or ultrasonic bonding. The side panels 34 and 134 can also be formed as a portion of a component of the composite structure 33, such as the outer cover 40 or the bodyside liner 42.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to a distal edge 68b of the back panel 134, as is best shown in FIGS. 2 and 3.

Each of the side panels 34 and 134 can include one or more individual, distinct pieces of material. In particular embodiments, for example, each side panel 34 and 134 can include first and second side panel portions that are joined at a seam, with at least one of the portions including an elastomeric material. Still alternatively, each individual side panel 34 and 134 can include a single piece of material which is folded over upon itself along an intermediate fold line (not shown).

The side panels 34 and 134 desirably include an elastic material capable of stretching. For example, the side panels 34 and 134 may stretch in a direction generally parallel to the transverse axis 49 of the training pant 20. In particular embodiments, the front and back side panels 34 and 134 may each include an interior portion 78 disposed between the distal edge 68a, 68b and the respective front or back center panel 35 or 135. In the illustrated embodiment in FIG. 3, the interior portions 78 are disposed between the distal edges 68a, 68b and the side edges 47 of the rectangular composite structure 33. The elastic material of the side panels 34 and 134 can be disposed in the interior portions 78 to render the side panels elastomeric in a direction generally parallel to the transverse axis 49. Most desirably, each side panel 34 and 134 is elastomeric from a waist end edge 72 to a leg end edge 70. More specifically, individual samples of side panel material, taken between the waist end edge 72 and the leg end edge 70 parallel to the transverse axis 49 and having a length from the attachment line 66 to the distal edge 68a, 68b and a width of about 2 centimeters, are all elastomeric.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 40 or bodyside liner 42, or stretchable but inelastic materials.

As shown in FIG. 1, the training pant 20 according to the present invention includes a pair of laterally opposing side seams 80 for securing each front side panel 34 to the corresponding back side panel 134. Desirably, the side seam 80 has a width of less than about 10 mm, more desirably about 2 mm to about 8 mm. In alternative embodiments, the side seam 80 may have a greater width, for example up to about 30 mm if desired. Further, the side seam 80 desirably extends from the waist opening 50 to one leg opening 52 between the front side panel 34 and the back side panel 134. In an alternative embodiment, the side seams 80 extend along a portion of the side panels 34 and 134 between the waist opening 50 and the leg openings 52. Desirably, the side seams 80 are concealed or hidden such that the side seams 80 are not visible or noticeable from the outer surface 30 of the training pant 20.

Figure 4A:
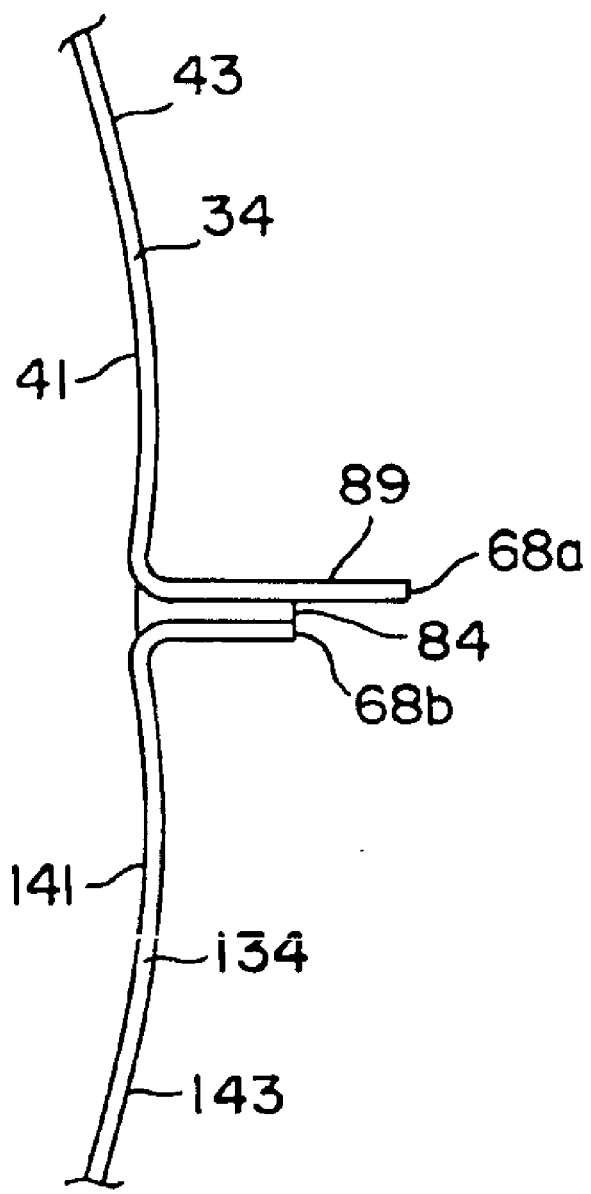
FIG. 4A illustrates a cross-sectional view of a standing offset butt seam which is not tacked down, according to one embodiment of this invention.
Figure 4B:
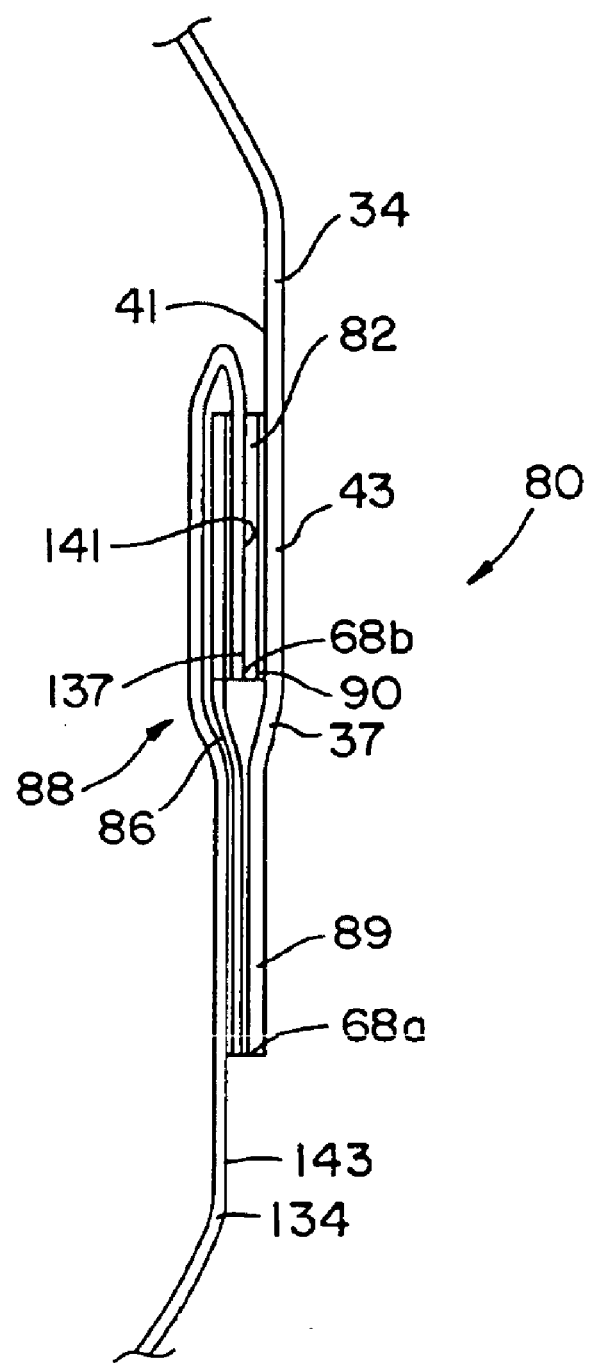
FIG. 4B illustrates a cross-sectional view of a tacked down offset butt side seam, according to one embodiment of this invention.
Figure 5:
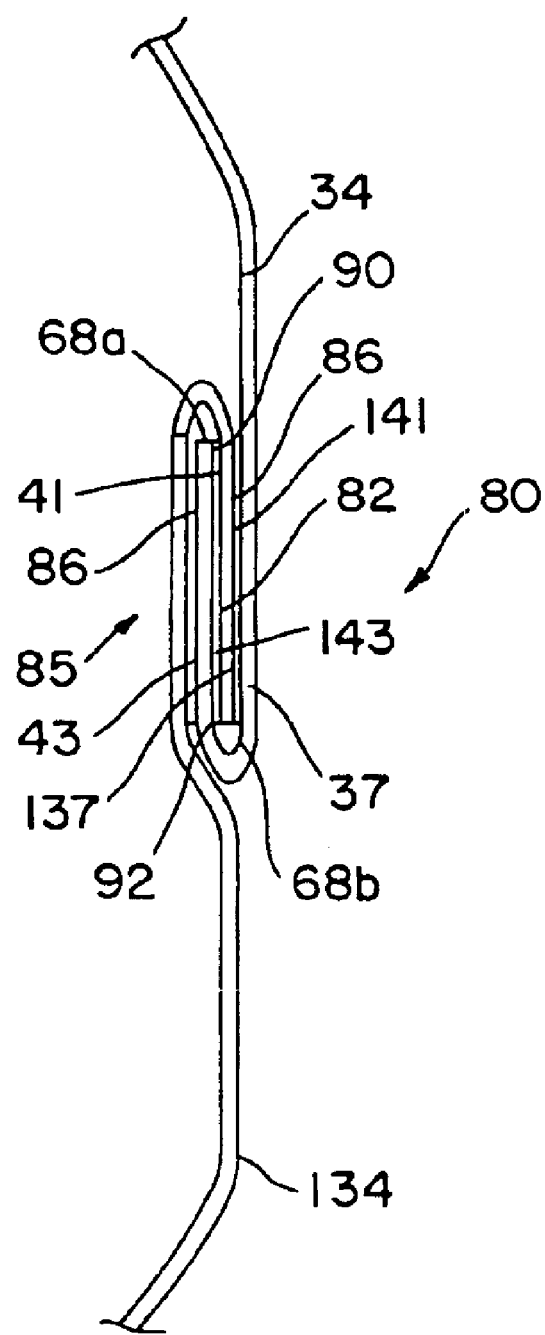
FIG. 5 illustrates a cross-sectional view of a side seam, according to one embodiment of this invention.

As shown in FIGS. 4A, 4B and 5, the front side panel 34 is connected to the back side panel 134 at the side seam 80 using conventional bonding means, such as adhesive bonding and/or ultrasonic bonding means. The side seam 80 includes a first or primary bond 82 and a second or secondary bond 86. Each of the primary bond 82 and the secondary bond 86 can include one bond or a series of similar or different bonds. Desirably, but not necessarily, the primary bond 82 and the secondary bond 86 are permanent bonds. The primary bond 82 and the secondary bond 86 are illustrated in FIGS. 4 and 5 as separate elements for clarity. However, it is apparent to one having ordinary skill in the art that the primary bond 82 and/or the secondary bond 86 may be regions of the side panels 34, 134, rather than separate elements (e.g. an ultrasonic bond region).

In one embodiment of this invention as shown in FIG. 4B, the primary bond 82, in combination with the secondary bond 86 discussed below, connects the edge portion 37 of the front side panel 34 to the edge portion 137 of the corresponding back side panel 134 to form a tacked down offset butt side seam 88. The primary bond 82 connects an inner surface 41 of the edge portion 37 to an inner surface 141 of the edge surface 137, as shown in FIG. 4B.

The term "tacked down offset butt side seam," as used herein, refers to a seam connecting the front side panel 34 and the back side panel 134 such that the front side panel 34 and the back side panel 134 are bonded together face-to-face or back-to-back in close proximity to an outer edge of each of the side panels 34 and 134 such that an offset portion 89 of one of the front side panel 34 and the back side panel 134 extends in a lateral direction outwardly from the primary bond 82. The offset butt side seams 88 experience a combination of a peel force at the primary bond 82 and a shearing strain during use, as opposed to peel forces, at the secondary bond 86 (discussed below), thereby reducing the likelihood of the side seams 88 opening unexpectedly.

In one embodiment, one of the front side panel 34 and the back side panel 134 is longer than the other side panel in a cross direction or lateral direction of the training pant 20. For example, as shown in FIG. 4A, the front side panel 34 is longer in the cross direction than the back side panel 134 to form an untacked down standing offset portion 89 of the front side panel 34, which can be bonded to the outer surface 143 of the back side panel 134 by the secondary bond 86, as discussed below. Desirably, the offset portion 89 has a width in the cross direction of about 2 mm to about 30 mm, more desirably about 3 mm to about 8 mm. Further, the offset portion 89 desirably extends along the entire length of the side seam 80 between the waist opening 50 and the leg opening 52.

The inner surface 41 of the edge portion 37 is bonded to the inner surface 141 of the edge portion 137 at a laterally inward distance from the distal edge 68a such that the distance between the distal edge 68a of the front side panel 34 and the distal edge 68b of the back side panel 134 and/or an outward edge 90 of the primary bond 82 is equal to the length of the offset portion 89. Desirably, the primary bond 82 is an adhesive bond or an ultrasonic bond and is positioned such that the outward edge 90 is about 4 mm to about 15 mm from the distal edge 68b. The primary bond 82 desirably extends inwardly from the outward edge 90 about 2 mm to about 30 mm, more desirably about 2 mm to about 8 mm. In alternative embodiments of this invention, it may be desirable that the primary bond 82 be as narrow as possible while still effectively connecting the edge portions 37 and 137.

In an alternative embodiment, the distal edge 68a of the front side panel 34 can be aligned evenly with the distal edge 68*b* of the back side panel 134 at an initial stage in the process to form a "butt seam." As used herein, the term "butt seam" refers to a seam wherein two separate pieces of substrate are bonded together face-to-face or back-to-back in close proximity to an outer edge of each of the pieces of substrate.

For example, the primary bond 82 connects the edge portion 37 of the front side panel to the edge portion 137 of the corresponding back side panel 134 to form the butt seam between the front side panel 34 and the rear side panel 134. More specifically, an inner surface 41 of the front side panel 34 at the edge portion 37 is bonded to an inner surface 141 of the back side panel 134 at the edge portion 137. Any suitable bonding means known to those having ordinary skill in the art can be used to bond the inner surface 41 to the inner surface 141. Desirably, the primary bond 82 is an adhesive bond, an ultrasonic bond or a combination thereof. The outward edge 90 of the primary bond 82 can be about 8 mm to about 30 mm, more desirably about 10 mm to about 15 mm, from the distal edges 68*a* and 68*b* of side panels 34 and 134, respectively, at an initial stage of the process. Desirably, the primary bond 82 has a width of about 2 mm to about 30 mm, more desirably about 2 mm to about 8 mm. After the primary bond 82 connects the edge portions 37 and 137, the material extending laterally outward beyond the primary bond 82 can be trimmed or removed such that the front side panel 34 is offset from the back side panel 134 to produce the offset portion 89. Desirably, the offset portion 89 has a width in the cross direction of about 2 mm to about 25 mm, more desirably about 3 mm to about 8 mm. The distance between the distal edge 68*b* of the back side panel 134 and the outward edge 90 of the primary bond 82 desirably is about 0 mm to about 15 mm. This alternative embodiment allows offsetting the side panels 34 and 134 to correct any misalignment due to the material weave-in process wherein it is difficult to evenly align the outer edges of the side panels 34 and 134.

The edge portion 137 can be folded flat with respect to the outer surface 143 of the back side panel 134 such that the front side panel 34 covers the edge portion 137 of the back side panel 134 and the outer surface 143 is in facing relationship with the inner surface 41 of the front side panel 34 at the offset portion 89. The offset portion 89 can be bonded to the outer surface 143 by the secondary bond 86, as shown in FIG. 4. The secondary bond 86 desirably, but not necessarily, extends from the front distal edge 68*a* to the back distal edge 68*b*. This secondary bond 86 may also extend about 1 mm to about 12 mm on either side (distal or proximal) of the front distal edge 68*a* and the back distal edge 68*b*. The edge portion 137 can be bonded to the folded over portion of the edge portion 137, thus, forming the side seam 80. The secondary bond 86 can include any suitable bond, such as an adhesive bond and/or an ultrasonic bond.

In an alternative embodiment of this invention, the back side panel 134 can be offset from the front side panel 34 and the offset portion 89 of the back side panel 134 can be bonded by the secondary bond 86 to the outer surface 43 of the front side panel 34 at the edge portion 37, after the front side panel 34 is folded so that the outer surface 43 of the front side panel 34 is in facing relationship with the inner surface 141 of the back side panel 134.

In one embodiment of this invention as shown in FIG. 5, the primary bond 82, in combination with the secondary bond 86 discussed below, connects the edge portion 37 of the front side panel to the edge portion 137 of the corresponding back side panel 134 to form a folded lap side seam 85, as shown in FIG. 5. The term "folded lap side seam," as used herein, refers to a seam connecting the front side panel 34 and the back side panel 134 such that the front side panel 34 and the back side panel 134 overlap and are folded with respect to each other at least once. The side seam 80 is located between the distal edges 68*a* of the front side panel 34 and the distal edge 68*b* of the back side panel 134. The folded lap side seams 85 initially experience a peel force during use, potentially followed by shearing forces during use, thereby reducing the likelihood of the seams opening unexpectedly.

The edge portions 37 and 137 can be overlapped sufficiently to allow the primary bond 82 to attach the side panels 34 and 134 together. Desirably, the front side panel 34 overlaps the back side panel 134 by a distance of about 2 mm to about 30 mm, more desirably about 4 mm to about 12 mm. More specifically, the inner surface 41 of the front side panel 34 at the edge portion 37 is bonded to the outer surface 143 of the back side panel 134 at the edge portion 137. Further, the front side panel 34 desirably overlaps the back side panel 134 along the entire length of the side seam 80 between the waist opening 50 and the leg opening 52. The overlap orientation provides a side seam 80 which does not have to be trimmed after the bonding process and, thus, reduces the material needed and the material wasted to produce side panels 34 and 134. Further, the overlap orientation limits the material which protrudes outwardly from a lateral surface of the training pant 20, after the side seam 80 is formed.

The inner surface 41 of the edge portion 37 is bonded to the outer surface 143 of the edge portion 137 by the primary bond 82 at a laterally inward distance from the distal edge 68*a* such that the distance between the distal edge 68*a* of the front side panel 34 and an outward edge 90 of the primary bond 82 is about 0 mm to about 12 mm. Desirably, the primary bond 82 is an adhesive bond, an ultrasonic bond or a combination thereof, having a width of less than about 30 mm, more desirably about 3 mm to about 8 mm. However, it is generally desirable that the width of the primary bond 82, as well as the secondary bond or bonds 86, are less than or equal to the distance that the front side panel 34 overlaps the back side panel 134. Any suitable bonding means known to those having ordinary skill in the art can be used to bond the inner surface 41 to the inner surface 141. In alternative embodiments of this invention, it may be desirable that the primary bond 82 be as narrow as possible while still effectively connecting the edge portions 37 and 137 together.

After the primary bond 82 connects the edge portions 37 and 137, the edge portion 137 can be folded along a length of the outward edge 90 of the primary bond 82 (which, in one embodiment, extends along the length of the side seam 80 from the waist opening 50 to the leg opening 52) onto the outer surface 43 of the front side panel 34 such that the outer surface 143 of the back side panel 134 contacts the outer surface 43 of the front side panel 34. The outer surface 143 can be bonded to the outer surface 43 by the secondary bond 86, as shown in FIG. 5. The secondary bond 86 desirably, but not necessarily, extends laterally along the edge portion 37 so that the width of the secondary bond 86 is about equal to the width of the primary bond 82. The secondary bond 86 can include any suitable bond, desirably an adhesive bond and/or an ultrasonic bond.

Additionally, the edge portion 37 can be folded along a length of an inward edge 92 of the primary bond 82 onto the inner surface 141 of the back side panel 134 such that the inner surface 41 of the front side panel 34 contacts the inner surface 141 of the back side panel 134, as shown in FIG. 5. The inner surface 41 can be bonded to the inner surface 141 using a second secondary bond 86. The secondary bond 86 desirably, but not necessarily, extends laterally along the edge portion 137 such that a width of the second secondary bond 86 is about equal to the width of the primary bond 82. The second secondary bond 86 can include any suitable bond, desirably an adhesive bond and/or an ultrasonic bond. In an alternative embodiment of this invention, the back side panel 134 can overlap the front side panel 34 to form the folded lap side seam 88, as described above.

As described herein, the various components of the training pant 20 can be integrally assembled together employing various types of suitable attachment means, such as adhesive, sonic and thermal bonds or combinations thereof. The resulting product is an absorbent garment having side seams connecting corresponding front side panels and back side panels, which are concealed to provide a finished, aesthetically pleasing appearance.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A disposable garment comprising:
   a front waist region, a back waist region, and a crotch region extending between the waist regions,
   a first side panel extending from the front waist region;
   a second side panel extending from the back waist region; and
   a side seam including a primary bond bonding an inner surface of the first side panel to an inner surface of an edge portion of the second side panel and forming an offset portion at an edge portion of the first side panel, and a secondary bond bonding the offset portion to an outer surface of the second side panel, the secondary bond extending to bond an outer surface of the second side panel edge portion to the outer surface of the second side panel.

2. The disposable garment of claim 1 wherein the side seam has a width of about 5 mm to about 8 mm.

3. The disposable garment of claim 1 wherein the primary bond has a width of less than about 30 mm.

4. The disposable garment of claim 1 wherein the primary bond has a width of about 2 mm to about 8 mm.

5. The disposable garment of claim 1 wherein the secondary bond has a width of less than about 30 mm.

6. The disposable garment of claim 1 wherein the secondary bond has a width of about 2 mm to about 8 mm.

7. The disposable garment of claim 1 wherein the side seam has a width of about 5 mm to about 30 mm.

8. A disposable garment, comprising:
   a chassis comprising a front side panel and a back side panel, and defining a waist opening and first and second leg openings;
   a first side seam extending from the waist opening to the first leg opening and connecting the front side panel and the back side panel; and
   a second side seam extending from the waist opening to the second leg opening and connecting the front side panel and the back side panel,
   each side seam having a width of about 5 mm to about 30 mm, and including a primary bond bonding an inner surface of the front side panel to an inner surface of an edge portion of the back side panel and forming an offset portion at an edge portion of the front side panel, and a secondary bond bonding the offset portion to an outer surface of the back side panel, the secondary bond extending to bond an outer surface of the back side panel edge portion to the outer surface of the back side panel.

9. The disposable garment of claim 8 wherein each side seam has a width of about 5 mm to about 8 mm.

10. The disposable garment of claim 8 wherein each primary bond has a width of less than about 30 mm.

11. The disposable garment of claim 8 wherein each primary bond has a width of about 2 mm to about 8 mm.

12. The disposable garment of claim 8 wherein each secondary bond has a width of less than about 30 mm.

13. The disposable garment of claim 8 wherein each secondary bond has a width of about 2 mm to about 8 mm.

14. The disposable garment of claim 8, wherein the front side panel comprises an offset portion having a width in a cross direction of about 2 mm to about 30 mm.

15. The disposable garment of claim 8 wherein the front side panel comprises an offset portion having a width in a cross direction of about 3 mm to about 8 mm.

16. The disposable garment of claim 8 wherein an inner surface of an edge portion of the front side panel is bonded to an outer surface of the back side panel.

17. A disposable garment comprising:
   a front waist region, a back waist region, and a crotch region extending between the waist regions,
   a first side panel extending from the front waist region;
   a second side panel extending from the back waist region; and
   a concealed side seam including a primary bond bonding an inner surface of the first side panel to an inner surface of an edge portion of the second side panel and forming an offset portion at an edge portion of the first side panel, and a secondary bond bonding the offset portion to an outer surface of the second side panel, the secondary bond extending to bond an outer surface of the second side panel edge portion to the outer surface of the second side panel, the concealed side seam having a width of about 5 mm to about 30 mm.

18. The disposable garment of claim 17 wherein the concealed side seam has a width of about 5 mm to about 8 mm.

19. The disposable garment of claim 17 wherein the primary bond has a width of less than about 30 mm.

20. The disposable garment of claim 17 wherein the primary bond has a width of about 2 mm to about 8 mm.

21. The disposable garment of claim 17 wherein the secondary bond has a width of less than about 30 mm.

22. The disposable garment of claim 17 wherein the secondary bond has a width of about 2 mm to about 8 mm.

* * * * *